(12) United States Patent
Suleiman et al.

(10) Patent No.: US 11,478,667 B2
(45) Date of Patent: *Oct. 25, 2022

(54) HAIR STYLING COMPOSITIONS HAVING SHEAR THICKENING PROPERTIES

(71) Applicant: L'OREAL, Paris (FR)

(72) Inventors: Azizah Khader Suleiman, Paterson, NJ (US); Anand Ramachandra Mahadeshwar, Scotch Plains, NJ (US); Anna Leticia M. Botto, Cranford, NJ (US); Emma Jean Naiberk, Hoboken, NJ (US); Vanessa Decarlo, Roselle Park, NJ (US)

(73) Assignee: L'OREAL, Paris (FR)

( * ) Notice: Subject to any disclaimer, the term of this patent is extended or adjusted under 35 U.S.C. 154(b) by 160 days.

This patent is subject to a terminal disclaimer.

(21) Appl. No.: 16/684,894

(22) Filed: Nov. 15, 2019

(65) Prior Publication Data

US 2020/0078613 A1 Mar. 12, 2020

Related U.S. Application Data

(63) Continuation of application No. 15/716,785, filed on Sep. 27, 2017, now Pat. No. 10,543,384.

(51) Int. Cl.
*A61Q 5/00* (2006.01)
*A61Q 5/06* (2006.01)
*A61K 8/73* (2006.01)
*A61K 8/81* (2006.01)
*A61Q 5/12* (2006.01)

(52) U.S. Cl.
CPC .......... *A61Q 5/06* (2013.01); *A61K 8/73* (2013.01); *A61K 8/732* (2013.01); *A61K 8/8152* (2013.01); *A61K 8/8158* (2013.01); *A61K 8/8182* (2013.01); *A61K 2800/594* (2013.01); *A61Q 5/00* (2013.01); *A61Q 5/12* (2013.01)

(58) Field of Classification Search
None
See application file for complete search history.

(56) References Cited

U.S. PATENT DOCUMENTS

| | | | |
|---|---|---|---|
| 7,179,451 B2 | 2/2007 | Brandt et al. | |
| 7,351,405 B2 | 4/2008 | De La Poterie | |
| 7,378,085 B2 | 5/2008 | Belli | |
| 8,252,271 B2 | 8/2012 | Singer et al. | |
| 8,399,001 B2 | 3/2013 | Laurent et al. | |
| 2001/0022967 A1 | 9/2001 | Brandt et al. | |
| 2004/0071652 A1 | 4/2004 | Dupuis et al. | |
| 2005/0118120 A1 | 6/2005 | Azizova et al. | |
| 2006/0134049 A1* | 6/2006 | Keenan | A61K 8/81 424/70.15 |
| 2007/0009463 A1* | 1/2007 | Niebauer | A61K 8/0237 424/70.7 |
| 2007/0134191 A1 | 6/2007 | Singer et al. | |
| 2009/0123405 A1 | 5/2009 | Sun et al. | |
| 2011/0054042 A1 | 3/2011 | Wu et al. | |
| 2014/0369947 A1* | 12/2014 | Pios | A61K 8/817 424/70.15 |
| 2015/0157543 A1 | 6/2015 | He et al. | |
| 2016/0128944 A1 | 5/2016 | Chawrai et al. | |
| 2017/0189306 A1 | 7/2017 | Van Nguyen et al. | |

OTHER PUBLICATIONS

International Search Report and Written Opinion dated Jan. 15, 2019 for corresponding PCT Application No. PCT/US2018/050443.
"XXL Body Ultra Strong Thickening Mousse", GNDP, MINTEL, Oct. 2012; XP002776283.
"Compositions with beneficial properties", IP. Com Journal, IP. Com Inc., West Henrietta, NY, US, Jul. 2011; XP013147352.
Joseph Shieh: "Lubrizol's Solution for Enhancing Fragrance Retention", IP. Com Journal, IP. Com Inc., West Henrietta, Ny, US, Mar. 2017; XP013174708.
"Soft Water Pomade—Baxter of California"—https://www.bloomingdales.com/shop/product/baxter-of-california-soft-water-pomade?ID=1769703&pla_country=US&cm_mmc=Google-PLA-ADC-_-Mens-Beauty%20Test-_-Baxter%20Of%20California-_-838364004026USA&CAWELAID=120156070003676575&CAGPSPN=pla&CAAGID=47685647199&CATCI=pla-387-016091652&gclid=EAIaIQobChMilPLDIYzd2AIVnUoNCh1Gb wghEAQYAiABEgKJGvD_BwE.
"Redken Stand Tough Extreme Gel"—https://www.walmart.com/ip/Redken-Stand-Tough-Extreme-Gel-5-Fl-Oz/34112179.
"Redken For Men Stand Tough Extreme Hold Gel-5oz by REDKEN"—http://surushop.com/index.php?route=product/product&product_id—16081.
"Garnier Fructis Style Root Amp Root Lifting Spray Mousse"—https://www.walmart.com/ip/Garnier-Fructis-Style-Root-Amp-Root-Lifting-Spray-Mousse-All-Hair-Types-5-oz-Packaging-May-Vary/41126916?wrnlspartner=wlpa&selectedSellerId=0&wl13=2258&adid=22222222227031204808&wl0=&wl1=g&wl2=c&wl3=53409007112&wl4=aud-273067695102:pla-88837145577&wl5=9007529&wl6=&wl7=&wl8=&wl9=pla&wl10=8175035&wl11=local&wl12=41126916&wl13=2258&veh=sem.
"Garnier Fructis Full & Plush Root Amp Spray Mousse"—https://www.walmart.com/ip/2-Pack-Garnier-Fructis-Full-Plush-Root-Amp-Spray-Mousse-5-oz/583651876?wrnlspartner=wlpa&selectedSellerId=1150&adid=22222222227076918651&wmlspartner=wrntiabs&wl0=&wl1=g&wl2=c&wl3=189655409440&wl4=aud-310687321802:pla-294784174269&wl5=9007529&wl6=&wl7=&wl8=&wl9=pla&wl10=112549851&wl11=online&wl12=583651876&wl13=&veh=sem.
"Garnier Fructis Style XXL Body Thickening Mousse"—https://www.amazon.com/Garnier-Fructis-Thickening-Mousse-Strong/dp/B00778LTDU.
"Redken Body Full Instant Bodifier Volumizing Foam"—https://www.ebay.com/p/Redken-Body-Full-Instant-Bodifier-Volumizing-Foam-5oz/7009476819.

\* cited by examiner

*Primary Examiner* — Susan T Tran
(74) *Attorney, Agent, or Firm* — Polsinelli PC

(57) ABSTRACT

The present disclosure relates to a hair styling compositions that exhibit non-Newtonian shear thickening behavior. The hair styling composition include: (a) about 0.1 to about 7 wt. % of AMP-acrylates/allyl methacrylate copolymer, based on the total weight of the hair styling composition; (b) one or more nonionic film-forming polymers; (c) one or more (Continued)

polysaccharides; (d) one or more nonionic surfactants; and (e) water. Additional components such as, for example, water-soluble solvents, fatty compounds, amphoteric film-forming polymers, volatile or non-volatile silicones, thickeners (ionic or non-ionic), etc., may also optionally be included. The hair styling compositions are particularly useful for styling or shaping hair and for providing hold, discipline, and texture to hair.

20 Claims, No Drawings

HAIR STYLING COMPOSITIONS HAVING SHEAR THICKENING PROPERTIES

CROSS-REFERENCE TO RELATED APPLICATIONS

This application is a continuation application of U.S. Ser. No. 15/716,785, filed Sep. 27, 2017, which is incorporated herein by reference in its entirety.

FIELD OF THE DISCLOSURE

The present disclosure relates to hair styling compositions that exhibit non-Newtonian shear thickening behavior during use by providing a liquid-to-solid transformation for easier application, while maintaining the key attributes of a traditional styling solid (i.e. clay, paste, pomade). The hair styling compositions are useful for styling or shaping the hair and for providing hold, discipline, and texture to the hair.

BACKGROUND

Consumers desire new multi-functional hair products that can not only impart good styling benefits to hair, but also simplify their routine by providing easier mechanisms of application and distribution onto the hair. Such products should be pleasing to the senses, have innovative, interesting and/or pleasing textures, without loss in functional performance. Furthermore, many consumers prefer hair products that are light in texture, easy to apply, and provide discipline/hold to the hair.

Traditional hair styling products on the cosmetic market appear in various forms. They range anywhere from solutions, foams, gels, creams, waxes, mousses, sprays, serums, to aerosols and can impart a variety of levels of protection and style to the hair depending on the state of the hair and the components of the product. Generally, products that are designed to impart styling or shaping benefits to hair are in the form of hair styling or hair care/hair treatment products. Such products are sometimes solids, or very thick/viscous, making them difficult to apply. Upon application, these product may dry unevenly due to the product format or become stiff and/or "crunchy" with limited hold (i.e. the film is overly hard and brittle), which is undesirable for many consumers.

Current products for imparting styling or shaping benefits to hair often include water soluble film-forming polymers. Depending on the chemical make-up of these polymers, they may be either soluble in water, or they may be water insoluble polymers which are made water soluble via various chemical modifications, such as neutralization. Solutions comprising these polymers tend to be viscous, i.e. as the concentration of the polymer increases, its viscosity builds up rapidly. Translated to styling applications, as the solvent evaporates, the polymer solution becomes thicker on the hair surface, resulting in a sticky or tacky film.

SUMMARY OF THE DISCLOSURE

The instant disclosure relates to hair styling compositions having unique rheological properties; the compositions exhibit non-Newtonian shear thickening behavior during use. The viscosity increases as a function of shear stress applied to the composition. Therefore, at rest or when the compositions are subjected to very little physical manipulation, the compositions are more "liquid-like." When the compositions are subjected to more vigorous physical manipulation, for example, when rubbed in the hand of a consumer and applied to the hair, the compositions become more "solid-like." In other words, the compositions exhibit a liquid-to-solid transformation during use. The hair styling compositions are particularly useful for providing the unique benefits solid styling products offer (such as clays and pastes), while being very easy to apply due to their distinctive rheology. For example, the compositions maintain the shape of hair, provide durable hold, and impart a pleasant texture and feel to hair, while being easy to apply due to their liquid-to-solid transformative behavior during use.

The hair styling compositions include:
  about 0.1 to about 7 wt. % of AMP-acrylates/allyl methacrylate copolymer, based on the total weight of the hair styling composition;
  one or more nonionic film-forming polymers and/or amphoteric film-forming polymer;
  one or more polysaccharides;
  one or more nonionic surfactants; and
  water.

While not wishing to be bound by any particular theory, the inventors believe that the unique non-Newtonian shear thickening behavior of the compositions is due in part to the combination of the AMP-acrylates/allyl methacrylate copolymer, the nonionic film-forming polymer(s) and/or amphoteric film-forming polymers, and the polysaccharide(s). The amount of AMP-acrylates/allyl methacrylate copolymer in the compositions may also be important. Interestingly, the amounts of AMP-acrylates/allyl methacrylate copolymer in the compositions was also found to influence the "holding" properties of the composition. AMP-acrylates/allyl methacrylate copolymer functions as a film-forming polymer in the instant compositions, and therefore contributes to the compositions' ability to "hold" the hair in a particular style or shape. The inventors found that lower amounts (less than about 7 wt. %) of the AMP-acrylates/allyl methacrylate copolymer actually resulted in better holding properties than higher amounts (greater than about 7 wt. %) of the AMP-acrylates/allyl methacrylate copolymer.

Non-limiting examples of nonionic film-forming polymers include vinylpyrrolidone homopolymers, copolymers of vinylpyrrolidone and of vinyl acetate, polyalkyloxazolines, vinyl acetate homopolymers, copolymers of vinyl acetate and of acrylic ester, copolymers of vinyl acetate and of ethylene, copolymers of vinyl acetate and of maleic ester, copolymers of polyethylene and of maleic anhydride, alkyl acrylate homopolymers and alkyl methacrylate homopolymers, acrylic ester copolymers, copolymers of acrylonitrile and of a non-ionic monomer, and a mixture thereof. In particular, the nonionic film-forming polymer(s) may be vinylpyrrolidone homopolymers, copolymers of vinylpyrrolidone and of vinyl acetate, and a mixture thereof. In some instances, a particularly useful nonionic film-forming polymer is polyvinylpyrrolidone/vinyl acetate (VP/VA) copolymer.

A non-limiting examples of an amphoteric film-forming polymers include octylacrlamide/acrylates/butylaminoethyl methacrylate copolymer.

Non-limiting examples of polysaccharides include celluloses (e.g., hydroxyethylcelluloses, hydroxypropylcelluloses, carboxymethylcelluloses) starches (including hydrolyzed starched and partially hydrolyzed starches), guar gums, inulins, xanthan gums, pullulan gums, agar-agar gums, carrageenan gums, gellan gums, gum arabics, tragacanth gums, xylans and derivatives thereof, cellobiose, maltodextrin, scleroglucan, chitosan, ulvan, fucoidan, alginate, pectin, heparin, hyaluronic acid, and a mixture thereof. In some cases, maltodextrin can be particularly useful.

Non-limiting examples of nonionic surfactants include hydrogenated castor oil, polysorbates, ethylene glycol ethers of fatty alcohols, polyethylene glycol derivatives of glycerides, polyoxyethylene alkyl ethers, alkyl polysaccharides, esters of polyols with fatty acids or alkoxylated derivatives thereof. More specific but non-limiting list of nonionic surfactants include PEG-40 hydrogenated castor oil, steareth-2, steareth-20, polysorbate 60, polyglyceryl-3 stearate, glyceryl stearate citrate, and a mixture thereof. In some instances, PEG-40 hydrogenated castor oil may be particularly useful.

Additional components may optionally be included in the hair styling compositions, for example, water-soluble solvents, fatty compounds, amphoteric film-forming polymers, volatile or nonvolatile silicones, as well as thickeners (ionic or non-ionic), etc. The types and amount of additional components can vary depending on the desired form of the hair styling composition. Non-limiting examples of hair styling compositions that may be mentioned include gels, pastes, clays, pomades, etc. Typically, the hair styling compositions are non-aerosol compositions. Non-aerosol compositions are free or essentially free of propellants such as, for example, propane, butane, isobutene, hydrofluorocarbon, dimethyl ether, and methyl ethyl ether.

The hair styling compositions may be used in various methods for treating hair, for example, human hair, including human hair one an individual's head. For example, the compositions are useful for: (i) improving or retaining curl definition or hold of hair; (ii) styling and shaping the hair; (iii) providing hair fiber alignment and discipline; and (iv) improving the appearance of hair; wherein the methods typically comprise applying a hair styling composition disclosed herein to the hair.

DETAILED DESCRIPTION OF THE DISCLOSURE

The instant disclosure relates to hair styling compositions that exhibit non-Newtonian shear thickening behavior and to and methods of using the hair styling compositions. Classical "Newtonian" fluids, as generally used herein, demonstrate a viscosity which is essentially independent of shear rate. "Non-Newtonian fluids," however, demonstrate a viscosity which either decreases or increases with increasing shear rate, e.g., the fluids are "shear thinning" or "shear thickening", respectively.

An example of a non-Newtonian fluid is a suspension of starch (flour) in water, sometimes called oobleck. Another non-Newtonian fluid is SILLY PUTTY, which is an example of a polymer based suspension. The application of force to some types of non-Newtonian fluids—for example by stabbing the surface with a finger, or rapidly inverting the container holding it-leads to the fluid behaving like a solid, rather than a liquid. Such non-Newtonian fluid is referred to as having a "shear thickening" property. More gentle treatment, such as slowly inserting a spoon, will leave it in its liquid state. Quickly pulling the spoon back out, however, triggers the return of the temporary solid state. Materials exhibiting such properties may be referred to as viscoelastic non-Newtonian fluids having shear thickening behavior. Non-Newtonian fluids, especially of multi-phase nature (foams, emulsions, dispersions and suspensions, slurries, for instance) and polymeric melts and solutions do not conform to the Newtonian postulate of the linear relationship between shear stress and shear rate in simple shear. Likewise, the apparent viscosity, defined as shear stress/shear rate, is not constant and is a function of shear stress or shear rate.

The viscosity of the hair styling compositions can be determined according to known methods for measuring viscosity. For example, a Ford viscosity cup viscometer can be used to determine the viscosity of Newtonian fluids according to testing methods provided under ASTM D 1200-94. A Ford viscosity cup viscometer can also be used to determine the viscosity of non-Newtonian fluids according to testing methods provided under ASTM D 2196. These and other methods of measuring viscosity are described in Viswanath, et al. *Viscosity of Liquids: Theory, Estimation, Experiment, and Data*, (Dordrecht: Springer, 2007).

The hair styling compositions of the instant disclosure typically include:
 about 0.1 to about 7 wt. % of AMP-acrylates/allyl methacrylate copolymer, based on the total weight of the hair styling composition;
 one or more nonionic film-forming polymers and/or one or more amphoteric film-forming polymers;
 one or more polysaccharides;
 one or more nonionic surfactants; and
 water;
 wherein the hair styling composition exhibits non-Newtonian shear thickening behavior.

As mentioned previously, AMP-acrylates/allyl methacrylate copolymer functions as a film-forming polymer, and therefore contributes to the hair styling compositions' ability to "hold" hair in a particular style or shape. It was surprisingly found that amounts (less than about 7 wt. %) of the AMP-acrylates/allyl methacrylate copolymer actually resulted in better holding properties than higher amounts (greater than about 7 wt. %) of the AMP-acrylates/allyl methacrylate copolymer. Accordingly, the total amount of the AMP-acrylates/allyl methacrylate copolymer in the hair styling compositions is typically about 0.1 to about 7 wt. %, based on the total weight of the hair styling composition.

In some instances, the total amount of the AMP-acrylates/allyl methacrylate copolymer in the hair styling compositions is about 0.1 to about 6 wt. %, about 0.1 to about 5 wt. %, about 0.1 to about 4 wt. %, about 0.5 to about 7 wt. %, about 0.5 to about 6 wt. %, about 0.5 to about 5 wt. %, about 0.5 to about 4 wt. %, about 1 to about 7 wt. %, about 1 to about 6 wt. %, about 1 to about 5 wt. %, about 1 to about 4 wt. %, about 2 to about 7 wt. %, about 2 to about 6 wt. %, about 2 to about 5 wt. %, about 2 to about 4 wt. %, or about 3 to about 4 wt. %, based on the total weight of the hair styling composition.

Non-limiting examples of nonionic film-forming polymers include vinylpyrrolidone homopolymers; copolymers of vinylpyrrolidone and of vinyl acetate; polyalkyloxazolines; vinyl acetate homopolymers; copolymers of vinyl acetate and of acrylic ester; copolymers of vinyl acetate and of ethylene; copolymers of vinyl acetate and of maleic ester; copolymers of polyethylene and of maleic anhydride; alkyl acrylate homopolymers and alkyl methacrylate homopolymers; acrylic ester copolymers; copolymers of acrylonitrile and of a non-ionic monomer; and a mixture thereof. In some cases, particularly useful nonionic film-forming polymers include vinylpyrrolidone homopolymers and copolymers of vinylpyrrolidone and of vinyl acetate, for example, polyvinylpyrrolidone/vinyl acetate (VP/VA) copolymer.

The nonionic film-forming polymers may be, for example, from: vinylpyrrolidone homopolymers; copolymers of vinylpyrrolidone and of vinyl acetate; polyalkyloxazolines, such as the polyethyloxazolines provided by the company Polymer Chemistry Innovations under the names Aquazol HP, and Aquzol HVIS; vinyl acetate homopolymers, such as the product provided under the name UCAR 130 Latex Resin by the company Dow Chemical or the product provided under the name Ultrapure Polymer 2041-R 012 by the company Ultra Chemical, Inc.; copolymers of vinyl acetate and of acrylic ester, such as the product provided under the name Rhodopas AD 310 from Rhone-Poulenc; copolymers of vinyl acetate and of ethylene, such as the product provided under the name Dermacryl LOR by the company Akzo Nobel; copolymers of vinyl acetate and of maleic ester, for example of dibutyl maleate, such as the product provided under the name Appretan MB Extra by the company Clariant; copolymers of polyethylene and of maleic anhydride; alkyl acrylate homopolymers and alkyl methacrylate homopolymers, such as the product provided under the name Micropearl RQ 750 by the company Matsumoto or the product provided under the name Luhydran® A 848 S by the company BASF; acrylic ester copolymers, such as, for example, copolymers of alkyl acrylates and of alkyl methacrylates, such as the product provided by the company Dow Chemical under the name Primal AC-261 K and the product provided by Evonik under the name Eudragit NE 30 D, by the company BASF under the names Acronal® 601, Luhydran R 8833 or 8845, or by the company Clariant under the names Appretan N 9213 or N9212; copolymers of acrylonitrile and of a non-ionic monomer chosen, for example, from butadiene and alkyl (meth)acrylates; mention may be made of the products provided under the names Nipol LX 531 B by the company Nippon Zeon or those provided under the name CJ 0601 B by the company Rohm and Haas; polyurethanes, such as the products provided under the names Acrysol RM 1020 or Acrysol RM 2020 by the company Dow Chemical or the products Uraflex XP 401 UZ or Uraflex XP 402 UZ by the company DSM Resins; copolymers of alkyl acrylate and of urethane, such as the product 8538-33 by the company National Starch; polyamides, such as the product Estapor LO 11 provided by the company Rhone-Poulenc; and chemically modified or unmodified non-ionic guar gums.

The unmodified non-ionic guar gums are, for example, the products sold under the name Vidogum GH by the company Unipectine and under the name Jaguar S by the company Rhodia. The modified non-ionic guar gums, which can be used according to the invention, are preferably modified by $C_1$-$C_6$ hydroxyalkyl groups. Mention may be made, by way of example, of the hydroxymethyl, hydroxyethyl, hydroxypropyl, and hydroxybutyl groups. These guar gums are well known in the state of the art and can, for example, be prepared by reacting the corresponding alkene oxides, such as, for example, propylene oxides, with guar gum, so as to obtain a guar gum modified by hydroxypropyl groups.

Other nonionic film forming polymers may be chosen from nonionic guar gums optionally modified by hydroxyalkyl groups are, for example, sold under the trade names Jaguar HP8, Jaguar HP60, Jaguar HP120, and Jaguar HP 105 by the company Rhodia or under the name Galactasol 4H4FD2 by the company Ashland Specialty Ingredients.

The alkyl radicals of the non-ionic fixing polymers have from 1 to 6 carbon atoms, unless otherwise mentioned.

In some instances, nonionic film forming polymers of the present disclosure are selected from the group consisting of vinylpyrrolidone homopolymers, copolymers of vinylpyrrolidone and of vinyl acetate, and a mixture thereof. Vinylpyrrolidone homopolymers (INCI name: polyvinylpyrrolidone) are commercially available from Ashland Specialty Ingredients under the tradename PVP K. Copolymers of vinylpyrrolidone and of vinyl acetate (INCI name: VP/VA copolymer) are commercially available from BASF under the tradename Luviskol VA.

The total amount of the one or more nonionic film-forming polymers may vary but is typically about 0.1 to about 20 wt. %, based on the total weight of the hair styling composition. In some cases, the total amount of the one or more nonionic film-forming polymers is about 0.1 to about 15 wt. %, about 0.1 to about 12 wt. %, about 0.1 to about 10 wt. %, about 0.1 to about 8 wt. %, about 0.1 to about 6 wt. %, about 0.5 to about 20 wt. %, about 0.5 to about 15 wt. %, about 0.5 to about 12 wt. %, about 0.5 to about 10 wt. %, about 0.5 to about 8 wt. %, about 0.5 to about 6 wt. %, about 1 to about 20 wt. %, about 1 to about 15 wt. %, about 1 to about 12 wt. %, about 1 to about 10 wt. %, about 1 to about 8 wt. %, or about 1 to about 6 wt. %, based on the total weight of the hair styling composition.

The hair styling composition may include one or more amphoteric film-forming polymers. The amphoteric film-forming polymers may be polymers containing units B and C distributed randomly in the polymer chain, in which B denotes a unit derived from a monomer containing at least one basic nitrogen atom and C denotes a unit derived from an acid monomer containing one or more carboxylic or sulphonic groups, or alternatively B and C can denote groups derived from carboxybetaine or sulphobetaine zwitterionic monomers;

B and C can also denote a cationic polymer chain containing primary, secondary, tertiary or quaternary amine groups, in which at least one of the amine groups bears a carboxylic or sulphonic group connected via a hydrocarbon radical or alternatively B and C form part of a chain of a polymer containing an $\alpha,\beta$-dicarboxylic ethylene unit in which one of the carboxylic groups has been made to react with a polyamine containing one or more primary or secondary amine groups.

The amphoteric film-forming polymers corresponding to the definition given above include the following polymers:

(1) polymers resulting from the copolymerization of a monomer derived from a vinyl compound bearing a carboxylic group such as, more particularly, acrylic acid, methacrylic acid, maleic acid, $\alpha$-chloroacrylic acid, and a basic monomer derived from a substituted vinyl compound containing at least one basic atom, such as, more particularly, dialkylaminoalkyl methacrylates and acrylates, dialkylaminoalkylmethacrylamides and -acrylamides;

(2) polymers containing units derived from:
  a) at least one monomer chosen from acrylamides and methacrylamides substituted on the nitrogen with an alkyl radical,
  b) at least one acidic comonomer containing one or more reactive carboxylic groups, and
  c) at least one basic comonomer such as esters containing primary, secondary, tertiary and quaternary amine substituents of acrylic and methacrylic acids and the product of quaternization of dimethylaminoethyl methacrylate with dimethyl or diethyl sulphate.

The N-substituted acrylamides or methacrylamides which may be useful are groups in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers include acrylic acid, methacrylic acid, crotonic acid, itaconic acid, maleic acid and fumaric acid and alkyl monoesters, having 1 to 4 carbon atoms, of maleic or fumaric acids or anhydrides.

In some cases, preferred basic comonomers are aminoethyl, butylaminoethyl, N,N'-dimethylaminoethyl and N-tert-butylaminoethyl methacrylates. Octylacrylamide/acrylates/butylaminoethyl methacrylate copolymer such as the products sold under the name Amphomer or Balance 47 (formerly Lovocryl 47) by the company Akzo Nobel can be used.

(3) crosslinked and alkylated polyamino amides partially or totally derived polyamino amides.

(4) polymers containing zwitterionic units of formula:

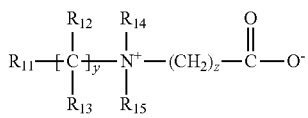

in which $R_{11}$ denotes a polymerizable unsaturated group, such as an acrylate, methacrylate, acrylamide or methacrylamide group, y and z represent an integer from 1 to 3, $R_{12}$ and $R_{13}$ represent a hydrogen atom or methyl, ethyl or propyl, and $R_{14}$ and $R_{15}$ represent a hydrogen atom or an alkyl radical such that the sum of the carbon atoms in $R_{14}$ and $R_{15}$ does not exceed 10.

The polymers comprising such units can also contain units derived from non-zwitterionic monomers such as dimethyl or diethylaminoethyl acrylate or methacrylate or alkyl acrylates or methacrylates, acrylamides or methacrylamides or vinyl acetate:

By way of example, mention may be made of the copolymer of methyl methacrylate/dimethyl carboxymethylammonio methyl ethyl methacrylate.

(5) Polymers derived from chitosan.
(6) Polymers derived from the N-carboxyalkylation of chitosan, such as N-carboxymethylchitosan or N-carboxybutylchitosan sold under the name "Evalsan" by the company Jan Dekker.
(7) Polymers corresponding to the general formula:

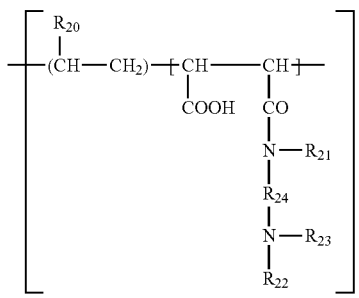

in which $R_{20}$ represents a hydrogen atom, a $CH_3O$, $CH_3CH_2O$ or phenyl radical, $R_{21}$ denotes hydrogen or a lower alkyl radical such as methyl or ethyl, $R_{22}$ denotes hydrogen or a lower alkyl radical such as methyl or ethyl, $R_{23}$ denotes a lower alkyl radical such as methyl or ethyl or a radical corresponding to the formula: —R.sub.24-N($R_{22}$).sub.2, $R_{24}$ representing a —$CH_2$—$CH_2$, —CH2-$CH_2$—$CH_2$— or —$CH_2$—$CH(CH_3)$— group, $R_{22}$ having the meanings mentioned above, as well as the higher homologues of these radicals and containing up to 6 carbon atoms.

(8) Alphoteric polymers of the type -D-X-D-X chosen from:
a) polymers obtained by the action of chloroacetic acid or sodium chloroacetate on compounds containing at least one unit of formula:

-D-X-D-X-D-     (I)

where D denotes a radical

and X denotes the symbol E or E', E or E', which may be identical or different, denotes a divalent radical which is an alkylene radical containing a straight or branched chain containing up to 7 carbon atoms in the main chain, which is unsubstituted or substituted with hydroxyl groups and which can contain, in addition to the oxygen, nitrogen and sulphur atoms, 1 to 3 aromatic and/or heterocyclic rings; the oxygen, nitrogen and sulphur atoms being present in the form of ether, thioether, sulphoxide, sulphone, sulphonium, alkylamine or alkenylamine groups, hydroxyl, benzylamine, amine oxide, quaternary ammonium, amide, imide, alcohol, ester and/or urethane groups.

b) Polymers of formula:

-D-X-D-X—     (I')

in which D denotes a radical

and X denotes the symbol E or E' and at least once E'; E having the meaning given above and E' is a divalent radical which is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain which is optionally interrupted by an oxygen atom and necessarily containing one or more carboxyl functions or one or more hydroxyl functions and betainized by reaction with chloroacetic acid or sodium chloroacetate.

(9) (C1-C5)alkyl vinyl ether/maleic anhydride copolymers, the maleic anhydride being partially modified by semiamidation with an N,N-dialkylaminoalkylamine such as N,N-dimethyl-aminopropylamine or by semiesterification with an N,N-dialkanolamine. These copolymers can also contain other vinyl comonomers such as vinylcaprolactam.

The amphoteric film-forming polymers which that may be particularly useful are those of family (3), such as the copolymers whose CTFA name is octylacrylamide/acrylates/butylaminoethyl methacrylate copolymer, such as the products sold under the names Amphomer LV 71 by the company Akzo Nobel.

In some instances, the one or more amphoteric film-forming polymers are selected from the group consisting of:
(i) polymers resulting from the copolymerization of a monomer derived from a vinyl compound bearing a carboxylic group selected from the group consisting of acrylic acid, methacrylic acid, maleic acid, and α-chloroacrylic acid, and a basic monomer derived from a substituted vinyl compound containing at least one basic atom;
(ii) polymers containing units derived from:
a) at least one monomer selected from the group consisting of acrylamides and methacrylamides substituted on the nitrogen with an alkyl radical, b) at least one acidic comonomer containing one or more reactive carboxylic groups, and
c) at least one basic comonomer ester containing primary, secondary, tertiary or quaternary amine substituents of acrylic and methacrylic acids or the product of quaternization of dimethylaminoethyl methacrylate with dimethyl or diethyl sulphate;
(iii) crosslinked and alkylated polyamino amides partially or totally derived polyamino amides; and
(vi) copolymers of methyl methacrylate/dimethyl carboxymethyl-ammoniomethylethylmethacrylate.

The total amount of the one or more amphoteric film-forming polymers may vary but is typically about 0.1 to about 20 wt. %, based on the total weight of the hair-styling composition. In some cases, the total amount of the one or more amphoteric film-forming polymers is about 0.1 to about 15 wt. %, about 0.1 to about 12 wt. %, about 0.1 to about 10 wt. %, about 0.1 to about 8 wt. %, about 0.5 to about 20 wt. %, about 0.5 to about 15 wt. %, about 0.5 to about 12 wt. %, about 0.5 to about 10 wt. %, about 0.5 to about 8 wt. %, about 1 to about 20 wt. %, about 1 to about 15 wt. %, about 1 to about 12 wt. %, about 1 to about 10 wt. %, or about 1 to about 8 wt. %, based on the total weight of the hair styling composition.

Polysaccharides are polymeric carbohydrate molecules composed of long chains of monosaccharide units bound together by glycosidic linkages and on hydrolysis give the constituent monosaccharides or oligosaccharides. They range in structure from linear to highly branched. Examples include storage polysaccharides such as starch and glycogen, and structural polysaccharides such as cellulose and chitin.

Polysaccharides are often quite heterogeneous, containing slight modifications of the repeating unit. Depending on the structure, these macromolecules can have distinct properties from their monosaccharide building blocks. When all the monosaccharides in a polysaccharide are the same type, the polysaccharide is called a homopolysaccharide or homoglycan, but when more than one type of monosaccharide is present they are called heteropolysaccharides or heteroglycans.

Non-limiting examples of polysaccharides include celluloses (e.g., hydroxyethylcelluloses, hydroxypropylcelluloses, carboxymethylcelluloses) starches (including hydrolyzed starched and partially hydrolyzed starches), guar gums, inulins, xanthan gums, pullulan gums, agar-agar gums, carrageenan gums, gellan gums, gum arabics, tragacanth gums, xylans and derivatives thereof, cellobiose, maltodextrin, scleroglucan, chitosan, ulvan, fucoidan, alginate, pectin, heparin, hyaluronic acid, and a mixture thereof. In some cases, maltodextrin can be particularly useful.

The total amount of the one or more polysaccharides can vary but is typically about 0.01 to about 15 wt. %, based on the total weight of the hair styling composition. In some cases, the total amount of the one or more polysaccharides is about 0.01 to about 12 wt. %, about 0.01 to about 10 wt. %, about 0.01 to about 8 wt. %, about 0.01 to about 5 wt. %, about 0.05 to about 15 wt. %, about 0.05 to about 12 wt. %, about 0.05 to about 10 wt. %, about 0.05 to about 8 wt. %, or about 0.05 to about 5 wt. %, based on the total weight of the hair styling composition.

Non-limiting examples of nonionic surfactants include the following:
(1) polyethylene oxide condensates of alkyl phenols, e.g., the condensation products of alkyl phenols having an alkyl group containing from about 6 to about 20 carbon atoms in either a straight chain or branched chain configuration, with ethylene oxide, the said ethylene oxide being present in amounts equal to from about 10 to about 60 moles of ethylene oxide per mole of alkyl phenol;
(2) those derived from the condensation of ethylene oxide with the product resulting from the reaction of propylene oxide and ethylene diamine products;
(3) condensation products of aliphatic alcohols having from about 8 to about 18 carbon atoms, in either straight chain or branched chain configurations, with ethylene oxide, e.g., a coconut alcohol ethylene oxide condensate having from about 10 to about 30 moles of ethylene oxide per mole of coconut alcohol, the coconut alcohol fraction having from about 10 to about 14 carbon atoms;
(4) long chain tertiary amine oxides of the formula $[R^1R^2R^3N \rightarrow O]$ where $R^1$ contains an alkyl, alkenyl or monohydroxy alkyl radical of from about 8 to about 18 carbon atoms, from 0 to about 10 ethylene oxide moieties, and from 0 to about 1 glyceryl moiety, and $R^2$ and $R^3$ contain from about 1 to about 3 carbon atoms and from 0 to about 1 hydroxy group, e.g., methyl, ethyl, propyl, hydroxyethyl, or hydroxypropyl radicals;
(5) long chain tertiary phosphine oxides of the formula $[RR'R''P \rightarrow O]$ where R contains an alkyl, alkenyl or monohydroxyalkyl radical ranging from about 8 to about 18 carbon atoms in chain length, from 0 to about 10 ethylene oxide moieties and from 0 to 1 glyceryl moieties and R' and R'' are each alkyl or monohydroxyalkyl groups containing from about 1 to about 3 carbon atoms;
(6) long chain dialkyl sulfoxides containing one short chain alkyl or hydroxy alkyl radical of from 1 to about 3 carbon atoms (usually methyl) and one long hydrophobic chain which include alkyl, alkenyl, hydroxy alkyl, or keto alkyl radicals containing from about 8 to about 20 carbon atoms, from 0 to about 10 ethylene oxide moieties and from 0 to 1 glyceryl moieties;
(7) alkyl polysaccharide (APS) surfactants (e.g. alkyl polyglycosides), including APS surfactants having a hydrophobic group with about 6 to about 30 carbon atoms and a polysaccharide (e.g., polyglycoside) as the hydrophilic group; optionally, there can be a polyalkylene-oxide group joining the hydrophobic and hydrophilic moieties; and the alkyl group (i.e., the hydrophobic moiety) can be saturated or unsaturated, branched or unbranched, and unsubstituted or substituted (e.g., with hydroxy or cyclic rings); a preferred material is alkyl polyglucoside, which is commercially available from Henkel, ICI Americas, and Seppic; and
(8) polyoxyethylene alkyl ethers such as those of the formula $RO(CH_2CH_2O)_nH$ and polyethylene glycol (PEG) glyceryl fatty esters, such as those of the formula $R(O)OCH_2CH(OH)CH_2(OCH_2CH_2)_nOH$, wherein n is from 1 to about 200, preferably from about 20 to about 100, and R is an alkyl having from about 8 to about 22 carbon atoms.

polyethylene glycol derivatives of glycerides as described in the above (8) useful herein include derivatives of mono-, di- and tri-glycerides and mixtures thereof. One class of polyethylene glycol derivatives of glycerides suitable herein is those which conform to the general formula (I):

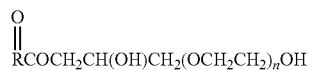

wherein n, the degree of ethoxylation, is from about 4 to about 200, preferably from about 5 to about 150, more preferably from about 20 to about 120, and wherein R comprises an aliphatic radical having from about 5 to about 25 carbon atoms, preferably from about 7 to about 20 carbon atoms. Suitable polyethylene glycol derivatives of glycerides can be polyethylene glycol derivatives of hydrogenated castor oil. Such polyethylene glycol derivatives of hydrogenated castor oil include, for example, PEG-20 hydrogenated castor oil, PEG-30 hydrogenated castor oil, PEG-40 hydrogenated castor oil, PEG-45 hydrogenated castor oil, PEG-50 hydrogenated castor oil, PEG-54 hydrogenated castor oil, PEG-55 hydrogenated castor oil, PEG-60 hydrogenated castor oil, PEG-80 hydrogenated castor oil, and PEG-100 hydrogenated castor oil.

Other suitable polyethylene glycol derivatives of glycerides can be polyethylene glycol derivatives of stearic acid. Such polyethylene glycol derivatives of stearic acid include, for example, PEG-30 stearate, PEG-40 stearate, PEG-50 stearate, PEG-75 stearate, PEG-90 stearate, PEG-100 stearate, PEG-120 stearate, and PEG-150 stearate.

Ethylene glycol ethers of fatty alcohols, as described in the above (3) or (8), useful herein include any ethylene glycol ethers of fatty alcohols which are suitable for use in a hair conditioning composition. No limiting examples of the ethylene glycol ethers of fatty alcohols include; the ceteth series of compounds such as ceteth-1 through ceteth-45, preferably ceteth-7 through ceteth-20; the isoceteth series of compounds such as isoceteth-20; the steareth series of compounds such as steareth-1 through 100; ceteareth 1 through ceteareth-50; the laureth series of compounds, preferably laureth-7 through Laureth-12; the pareth series of compounds, preferably pareth-9 through pareth-15; propylene glycol ethers of the above ceteth, steareth, ceteareth, and laureth series of compounds, such propylene glycol ethers of ceteth series of compounds including, for example, PPG-5-Ceteth-20; polyoxyethylene ethers or polyoxyethylene-polyoxypropylene ethers of branched alcohols, such branched alcohols including, for example, octyldodecyl alcohol, decyltetradecyl alcohol, dodecylpentadecyl alcohol, hexyldecyl alcohol, and isostearyl alcohol, and such polyoxyethylene-polyoxypropylene ethers of branched alcohols including, for example, POE(20)POP(6) decyltetradecyl ether; and mixtures thereof.

Other nonionic surfactants useful herein include, for example, polysorbates such as polysorbate-20 (POE(20) sorbitan monolaurate) having HLB value of 16.7, polysorbate-21 (POE(4) sorbitan monolaurate) having HLB value of 13.3, polysorbate-40 (POE(20) sorbitan monopalmitate) having HLB value of 15.6, polysorbate-60 (POE(20) sorbitan monostearate) having HLB value of 14.9, polysorbate-61 (POE(4) sorbitan monostearate) having HLB value of 9.6, polysorbate-80 (POE(20)sorbitan monooleate) having HLB value of 15.0, and polysorbate-81 (POE(4) sorbitan monooleate) having HLB value of 10.0.

In one embodiment, one or more nonionic surfactants are selected from the group consisting of PEG-40 hydrogenated castor oil, steareth-2, steareth-20, polysorbate 60, polyclyceryl-3 stearate, glyceryl stearate citrate, and a mixture thereof. In some instances, the one or more nonionic surfactants includes PEG-40 hydrogenated castor oil.

The total amount of the one or more nonionic surfactants can vary but is typically about 0.5 to about 20 wt. %, based on the total weight of the hair styling composition. In some cases, the total amount of the one or more nonionic surfactants is about 0.5 to about 15 wt. %, about 0.5 to about 12 wt. %, about 0.5 to about 10 wt. %, about 0.5 to about 8 wt. %, about 1 to about 20 wt. %, about 1 to about 15 wt. %, about 1 to about 12 wt. %, about 1 to about 10 wt. %, or about 1 to about 8 wt. %, based on the total weight of the hair styling composition.

The hair styling compositions often include one or more water-soluble solvents. The term "water-soluble solvent" is interchangeable with the term "water-miscible solvent" and means a compound that is liquid at 25° C. and at atmospheric pressure (760 mmHg), and it has a solubility of at least 50% in water under these conditions. In some cases, the water soluble solvent has a solubility of at least 60%, 70%, 80%, or 90%. Non-limiting examples of water-soluble solvents include, for example, glycerin, $C_{1-4}$ alcohols, organic solvents, polyols, glycols, and a mixture thereof.

As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. Other suitable examples of organic solvents are ethylene glycol, propylene glycol, butylene glycol, hexylene glycol, propane diol, and glycerin. The organic solvents can be volatile or non-volatile compounds.

Further non-limiting examples of water-soluble solvents include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, (caprylyl glycol), 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and a mixture thereof.

In some cases, the water-soluble solvent may be selected from the group consisting of one or more glycols, $C_{1-4}$ alcohols, glycerin, and a mixture thereof. In some cases, the water-soluble solvent is selected from the group consisting of hexylene glycol, proplene glycol, caprylyl glycol, glycerin, ethanol, isopropyl alcohol, and a mixture thereof. In some instances, the one or more water-soluble solvents are selected from the group consisting of polyhydric alcohols, glycol ethers, $C_{1-4}$ alcohols, and a mixture thereof.

Polyhydric alcohols are useful. Examples of polyhydric alcohols include glycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof. Polyol compounds may also be used. Non-limiting examples include the aliphatic diols, such as 2-ethyl-2-methyl-1,3-propanediol, 3,3-dimethyl-1,2-butanediol, 2,2-diethyl-1,3-propanediol, 2-methyl-2-propyl-1,3-propanediol, 2,4-dimethyl-2,4-pentanediol, 2,5-dimethyl-2,5-hexanediol, 5-hexene-1,2-diol, and 2-ethyl-1,3-hexanediol, and a mixture thereof.

The total amount of the one or more water-soluble solvents may vary but is typically about 0.1 to about 25 wt. %, based on the total weight of the hair styling composition. In some cases, the total amount of the one or more water-soluble solvents is about 0.1 to about 10 wt. %, about 0.1 to about 15 wt. %, about 0.1 to about 12 wt. %, about 0.1 to about 10 wt. %, about 1 to about 25 wt. %, about 1 to about 20 wt. %, about 1 to about 15 wt. %, about 1 to about 12 wt. %, about 1 to about 10 wt. %, about 2 to about 20 wt. %, about 2 to about 15 wt. %, or about 2 to about 10 wt. %, based on the total weight of the hair styling composition.

In some instances, the hair styling compositions may include one or more fatty compounds. Non-limiting examples of fatty compounds include oils, mineral oil, fatty alcohols, fatty acids, fatty alcohol derivatives, fatty acid derivatives (such as alkoxylated fatty acids or polyethylene glycol esters of fatty acids or propylene glycol esters of fatty acids or butylene glycol esters of fatty acids or esters of neopentyl glycol and fatty acids or polyglycerol/glycerol esters of fatty acids or glycol diesters or diesters of ethylene glycol and fatty acids or esters of fatty acids and fatty alcohols, esters of short chain alcohols and fatty acids), esters of fatty alcohols, hydroxy-substituted fatty acids, waxes, triglyceride compounds, lanolin, and a mixture thereof. For instance, one or more fatty compounds may be selected from the group consisting of ozokerite, cetearyl alcohol, tribehenin, stearyl alcohol, petrolatum, C12-14 isoparaffin, C12-15 alkyl benzoate, and a mixture thereof.

Non-limiting examples of the fatty alcohols, fatty acids, fatty alcohol derivatives, and fatty acid derivatives are found in International Cosmetic Ingredient Dictionary, Sixteenth Edition, 2016, which is incorporated by reference herein in its entirety.

Fatty alcohols useful herein include those having from about 10 to about 30 carbon atoms, from about 12 to about 22 carbon atoms, and from about 16 to about 22 carbon atoms. These fatty alcohols can be straight or branched chain alcohols and can be saturated or unsaturated. Nonlimiting examples of fatty alcohols include decyl alcohol, undecyl alcohol, dodecyl, myristyl, cetyl alcohol, stearyl alcohol, isostearyl alcohol, isocetyl alcohol, behenyl alcohol, linalool, oleyl alcohol, cholesterol, cis4-t-butylcyclohexanol, myricyl alcohol and a mixture thereof. In some cases, the fatty alcohols are those selected from the group consisting of cetyl alcohol, stearyl alcohol, isostearyl alcohol, oleyl alcohol, and a mixture thereof.

Fatty acids useful herein include those having from about 10 to about 30 carbon atoms, from about 12 to about 22 carbon atoms, and from about 16 to about 22 carbon atoms. These fatty acids can be straight or branched chain acids and can be saturated or unsaturated. Also included are diacids, triacids, and other multiple acids which meet the carbon number requirement herein. Also included herein are salts of these fatty acids. Nonlimiting examples of fatty acids include lauric acid, palmitic acid, stearic acid, behenic acid, arichidonic acid, oleic acid, isostearic acid, sebacic acid, and a mixture thereof. In some cases, the fatty acids are selected from the group consisting of palmitic acid, stearic acid, and a mixture thereof.

Fatty alcohol derivatives include alkyl ethers of fatty alcohols, alkoxylated fatty alcohols, alkyl ethers of alkoxylated fatty alcohols, esters of fatty alcohols and a mixture thereof. Nonlimiting examples of fatty alcohol derivatives include materials such as methyl stearyl ether; 2-ethylhexyl dodecyl ether; stearyl acetate; cetyl propionate; the ceteth series of compounds such as ceteth-1 through ceteth-45, which are ethylene glycol ethers of cetyl alcohol, wherein the numeric designation indicates the number of ethylene glycol moieties present; the steareth series of compounds such as steareth-1 through 10, which are ethylene glycol ethers of steareth alcohol, wherein the numeric designation indicates the number of ethylene glycol moieties present; ceteareth 1 through ceteareth-10, which are the ethylene glycol ethers of ceteareth alcohol, i.e. a mixture of fatty alcohols containing predominantly cetyl and stearyl alcohol, wherein the numeric designation indicates the number of ethylene glycol moieties present; C1-C30 alkyl ethers of the ceteth, steareth, and ceteareth compounds just described; polyoxyethylene ethers of branched alcohols such as octyldodecyl alcohol, dodecylpentadecyl alcohol, hexyldecyl alcohol, and isostearyl alcohol; polyoxyethylene ethers of behenyl alcohol; PPG ethers such as PPG-9-steareth-3, PPG-11 stearyl ether, PPG8-ceteth-1, and PPG-10 cetyl ether; and a mixture thereof.

Non-limiting olyglycerol esters of fatty acids include those of the following formula:

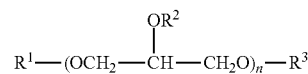

wherein the average value of n is about 3 and $R^1$, $R^2$ and $R^3$ each may independently be a fatty acid moiety or hydrogen, provided that at least one of $R^1$, $R^2$, and $R^3$ is a fatty acid moiety. For instance, $R^1$, $R^2$ and $R^3$ may be saturated or unsaturated, straight or branched, and have a length of $C_1$-$C_{40}$, $C_1$-$C_{30}$, $C_1$-$C_{25}$, or $C_1$-$C_{20}$, $C_1$-$C_{16}$, or $C_1$-$C_{10}$. For example, nonionic polyglycerol esters of fatty acids include polyglyceryl-5 laurate, The fatty acid derivatives are defined herein to include fatty acid esters of the fatty alcohols as defined above, fatty acid esters of the fatty alcohol derivatives as defined above when such fatty alcohol derivatives have an esterifiable hydroxyl group, fatty acid esters of alcohols other than the fatty alcohols and the fatty alcohol derivatives described above, hydroxy-substituted fatty acids, and a mixture thereof. Nonlimiting examples of fatty acid derivatives include ricinoleic acid, glycerol monostearate, 12-hydroxy stearic acid, ethyl stearate, cetyl stearate, cetyl palmitate, polyoxyethylene cetyl ether stearate, polyoxyethylene stearyl ether stearate, polyoxyethylene lauryl ether stearate, ethyleneglycol monostearate, polyoxyethylene monostearate, polyoxyethylene distearate, propyleneglycol monostearate, propyleneglycol distearate, trimethylolpropane distearate, sorbitan stearate, polyglyceryl stearate, dimethyl sebacate, PEG-15 cocoate, PPG-15 stearate, glyceryl monostearate, glyceryl distearate, glyceryl tristearate, PEG-8 laurate, PPG-2 isostearate, PPG-9 laurate, and a mixture thereof. Preferred for use herein are glycerol monostearate, 12-hydroxy stearic acid, and a mixture thereof.

In some cases, the one or more fatty compounds may be one or more high melting point fatty compounds. A high melting point fatty compound is a fatty compound having a melting point of 25° C. Even higher melting point fatty compounds may also be used, for example, fatty compounds having a melting point of 40° C. or higher, 45° C. or higher, 50° C. or higher. The high melting point fatty compound may be selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifteenth Edition, 2014, which is incorporated herein by reference in its entirety. The fatty alcohols useful herein are those having from about 14 to about 30 carbon atoms, preferably from about 16 to about 22 carbon atoms. These fatty alcohols are saturated and can be straight or branched chain alcohols. Non-limiting examples of high melting point fatty compounds include fatty alcohols such as, for example, cetyl alcohol (having a melting point of about 56° C.), stearyl alcohol (having a melting point of about 58-59° C.), behenyl alcohol (having a melting point of about 71° C.), and mixtures thereof. These compounds are known to have the above melting point. However, they often have lower melting points when supplied, since such supplied products are often mixtures of fatty alcohols having alkyl chain length distribution in which the main alkyl chain is cetyl, stearyl or behenyl group. In the present application, more preferred fatty alcohols are cetyl alcohol, stearyl alcohol and mixtures thereof.

The total amount of the one or more fatty compounds can vary, especially depending on the form of product desired. For example, liquid pastes and/or liquid clays may include higher amounts of fatty compounds that liquid pomades and liquid gels (liquid gels may be free or essentially free of fatty compounds). In any event, the total amount of the one or more fatty compounds, when present, may be about 0.1 to about 25 wt. %, based on the total weight of the hair styling composition. In some cases, the total amount of the one or more fatty compounds is about 0.1 to about 20 wt. %, about 0.1 to about 15 wt. %, about 0.1 to about 12 wt. %, about 0.1 to about 10 wt. %, about 0.5 to about 25 wt. %, about 0.5 to about 20 wt. %, about 0.5 to about 15 wt. %, about 0.5 to about 12 wt. %, about 0.5 to about 10 wt. %, about 1 to about 25 wt. %, about 1 to about 20 wt. %, about 1 to about 15 wt. %, about 1 to about 12 wt. %, or about 1 to about 10 wt. %, based on the total weight of the hair styling composition.

The hair styling composition may be in a variety of different forms, for example, a liquid gel, a liquid paste, a liquid clay, a liquid pomade, etc. The terms "gel," "paste," "clay," and "pomade," are used in conjunction with the term "liquid," due to the unique non-Newtonian shear thickening properties of the compositions. The compositions may be more fluid (have less viscosity) than typical gels, pastes, clays, pomades, etc., when at rest (or when subjected to only light shear force), but when subjected to more rigorous physical manipulation (when subjected to stronger shear force such as rubbing product in palms or hands) the compositions transform into a more solid consistency, which may be more typical of a classical gel, paste, clay, pomade, etc. The liquid paste, the liquid clay, and the liquid pomade of the instant disclosure may be in the form of an emulsion. The liquid gel of the instant disclosure is typically not in the form of an emulsion.

Viscosity measurements of the hair styling compositions may be carried out using Brookfield [RV] viscometer. The hair styling compositions typically have a viscosity of about 5000 mPas (cP) or less at room temperature (25° C.) (Torque 36.5% RPM 10, Spindle 3). In some cases, the viscosity may be about 4000 mPas (cP) or less, about 3500 mPas (cP) or less, about 3000 mPas (cP) or less, about 2500 mPas (cP) or less, about 2000 mPas (cP) or less, about 1500 mPas (cP) or less, about 1000 mPas (cP) or less, or about 500 mPas (cP) or less. These viscosity values relate to the "liquid" form of the compositions. In some cases with varying torques and spindles, the hair styling composition has a viscosity of about 1000 to about 1500 mPas (cP) (or about 1290) mPas (cP) at room temperature (25° C.) (Torque 16%, RPM 50, Spindle 5), or a viscosity of about 1100 to about 1600 mPas (cP) (or about 1340 mPas (cP)) at room temperature (25° C.) (Torque 67.4%, RPM 50, Spindle 3). Typically the liquid pastes of the instant disclosure have the highest viscosities. There is not necessarily a minimum viscosity for the hair styling compositions because some compositions (e.g., some of the liquid gels) are very thin (not-viscous) and therefore do not have a viscosity measurement. The viscosity of the liquid clays and the liquid pomades usually falls between the liquid gels and the liquid pastes.

In one embodiment, the hair styling compositions include:

(a) about 0.1 to about 7 wt. %, about 0.5 to about 6 wt. %, and about 1 to about 5 wt. % of AMP-acrylates/allyl methacrylate copolymer;

(b) about 0.1 to about 10 wt. %, about 0.5 to about 8 wt. %, or about 1 to about 6 wt. % of polyvinylpyrrolidone/vinyl acetate (VP/VA) copolymer;

(c) about 0.01 to about 10 wt. %, about 0.05 to about 8 wt. %, or about 0.05 to about 5 wt. % of maltodextrin;

(d) about 0.1 to about 15 wt. %, about 0.1 to about 12 wt. %, or about 1 to about 10 wt. % of one or more nonionic surfactants;

(e) about 60 to about 92 wt. % of water, about 65 to about 92 wt. %, or about 65 to about 90 wt. % water; and (f) about 1 to about 25 wt. %, about 1 to about 20 wt. %, or about 1 to about 15 wt. % of one or more water-soluble solvents comprising polyhydric alcohols.

The hair styling composition exhibits non-Newtonian shear thickening behavior and may be in the form of a liquid gel. Furthermore, the liquid gel may be free or essentially free of fatty compounds. For example, the liquid gel may be free or essentially free of oils, mineral oils, vegetable oils, fatty alcohols, fatty acids, hydroxy-substituted fatty acids, waxes, triglycerides, lanolins, alkanes, petrolatum, paraffins, and a mixture thereof.

More specifically, in some instances, the hair styling composition may include:

(a) about 0.1 to about 7 wt. %, about 1 to about 6 wt. %, or about 1 to about 5 wt. % of AMP-acrylates/allyl methacrylate copolymer;

(b) about 0.1 to about 8 wt. %, about 0.5 to about 7 wt. %, or about 1 to about 6 wt. % of polyvinylpyrrolidone/vinyl acetate (VP/VA) copolymer;

(c) about 0.01 to about 10 wt. %, about 0.05 to about 8 wt. %, or about 0.05 to about 5 wt. % of maltodextrin;

(d) about 0.1 to about 10 wt. %, about 0.5 to about 8 wt. %, or about 1 to about 5 wt. % of PEG-40 hydrogenated castor oil;

(e) about 60 to about 92 wt. % of water, about 65 to about 92 wt. %, or about 65 to about 90 wt. % water; and (f) about 1 to about 25 wt. %, about 1 to about 20 wt. %, or about 1 to about 15 wt. % of one or more water-soluble solvents comprising polyhydric alcohols selected from the group consisting of glycerin, ethylhexylglycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof.

The hair styling composition exhibits non-Newtonian shear thickening behavior and may be in the form of a liquid gel. Furthermore, the liquid gel may be free or essentially free of fatty compounds. For example, the liquid gel may be free or essentially free of oils, mineral oils, vegetable oils, fatty alcohols, fatty acids, hydroxy-substituted fatty acids, waxes, triglycerides, lanolins, alkanes, petrolatum, paraffins, and a mixture thereof.

In another embodiment, the hair styling compositions include:

(a) about 0.1 to about 7 wt. %, about 0.5 to about 6 wt. %, and about 1 to about 5 wt. % of AMP-acrylates/allyl methacrylate copolymer;

(b) about 0.1 to about 10 wt. %, about 0.5 to about 8 wt. %, or about 1 to about 6 wt. % of polyvinylpyrrolidone/vinyl acetate (VP/VA) copolymer;

(c) about 0.01 to about 10 wt. %, about 0.05 to about 8 wt. %, or about 0.05 to about 5 wt. % of maltodextrin;

(d) about 0.1 to about 15 wt. %, about 0.1 to about 12 wt. %, or about 1 to about 10 wt. % of one or more nonionic surfactants;

(e) about 50 to about 90 wt. % of water, about 50 to about 85 wt. %, or about 55 to about 85 wt. % water;

(f) about 1 to about 25 wt. %, about 1 to about 20 wt. %, or about 1 to about 15 wt. % of one or more water-soluble solvents comprising polyhydric alcohols; and (g) about 0.1 to about 20 wt. %, about 0.5 to about 15 wt. %, or about 1 to about 15 wt. % of one or more fatty compounds.

The hair styling composition exhibits non-Newtonian shear thickening behavior and may be in the form of a liquid paste. Furthermore, the liquid paste may include one or more conditioning agents, for example, bis-diglyceryl polyacyladipate-2, PEG-40/PPG-8 methylaminopropyl/hydroxypropyl dimethicone copolymer, and a mixture thereof.

More specifically, in some instances, the hair styling composition may include:

(a) about 0.1 to about 7 wt. %, about 0.5 to about 6 wt. %, and about 1 to about 5 wt. % of AMP-acrylates/allyl methacrylate copolymer;

(b) about 0.1 to about 10 wt. %, about 0.5 to about 8 wt. %, or about 1 to about 6 wt. % of polyvinylpyrrolidone/vinyl acetate (VP/VA) copolymer;

(c) about 0.01 to about 10 wt. %, about 0.05 to about 8 wt. %, or about 0.05 to about 5 wt. % of maltodextrin;

(d) about 0.1 to about 15 wt. %, about 0.1 to about 12 wt. %, or about 1 to about 10 wt. % of one or more nonionic surfactants selected from the group consisting of PEG-40 hydrogenated castor oil, polysorbate 60, steareth-2, steareth-20, and a mixture thereof;

(e) about 50 to about 90 wt. % of water, about 50 to about 85 wt. %, or about 55 to about 85 wt. % water;

(f) about 1 to about 25 wt. %, about 1 to about 20 wt. %, or about 1 to about 15 wt. % of one or more water-soluble solvents comprising polyhydric alcohols selected from the group consisting of glycerin, ethylhexylglycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof; and (g) about 0.1 to about 20 wt. %, about 0.5 to about 15 wt. %, or about 1 to about 15 wt. % of one or more fatty compounds selected from the group consisting of ozokerite, cetearyl alcohol, tribehenin, stearyl alcohol, petrolatum, and a mixture thereof.

The hair styling composition exhibits non-Newtonian shear thickening behavior and may be in the form of a liquid paste. Furthermore, the liquid paste may include one or more conditioning agents, for example, bis-diglyceryl polyacyladipate-2, PEG-40/PPG-8 methylaminopropyl/hydroxypropyl dimethicone copolymer, and a mixture thereof.

In another embodiment, the hair styling compositions include:

(a) about 0.1 to about 7 wt. %, about 0.5 to about 6 wt. %, and about 1 to about 5 wt. % of AMP-acrylates/allyl methacrylate copolymer;

(b) about 0.1 to about 10 wt. %, about 0.5 to about 8 wt. %, or about 1 to about 6 wt. % of octylacrylamide/acrylates/butylaminoethyl methacrylate copolymer;

(c) about 0.1 to about 15 wt. %, about 0.5 to about 10 wt. %, or about 1 to about 8 wt. % of maltodextrin;

(d) about 0.1 to about 15 wt. %, about 0.1 to about 12 wt. %, or about 1 to about 10 wt. % of one or more nonionic surfactants;

(e) about 50 to about 90 wt. % of water, about 50 to about 85 wt. %, or about 55 to about 85 wt. % water;

(f) about 1 to about 25 wt. %, about 1 to about 20 wt. %, or about 1 to about 15 wt. % of one or more water-soluble solvents comprising polyhydric alcohols; and (g) about 0.1 to about 20 wt. %, about 0.5 to about 15 wt. %, or about 1 to about 15 wt. % of one or more fatty compounds.

The hair styling composition exhibits non-Newtonian shear thickening behavior and may be in the form of a liquid paste. Furthermore, the liquid paste may include one or more conditioning agents, for example, bis-diglyceryl polyacyladipate-2, PEG-40/PPG-8 methylaminopropyl/hydroxypropyl dimethicone copolymer, and a mixture thereof.

More specifically, in some instances, the hair styling composition may include:

(a) about 0.1 to about 7 wt. %, about 0.5 to about 6 wt. %, and about 1 to about 5 wt. % of AMP-acrylates/allyl methacrylate copolymer;

(b) about 0.1 to about 10 wt. %, about 0.5 to about 8 wt. %, or about 1 to about 6 wt. % of octylacrylamide/acrylates/butylaminoethyl methacrylate copolymer;

(c) about 0.1 to about 15 wt. %, about 0.5 to about 10 wt. %, or about 1 to about 8 wt. % of maltodextrin;

(d) about 0.1 to about 15 wt. %, about 0.1 to about 12 wt. %, or about 1 to about 10 wt. % of one or more nonionic surfactants selected from the group consisting of PEG-40 hydrogenated castor oil, polysorbate 60, steareth-2, steareth-20, and a mixture thereof;

(e) about 50 to about 90 wt. % of water, about 50 to about 85 wt. %, or about 55 to about 85 wt. % water;

(f) about 1 to about 25 wt. %, about 1 to about 20 wt. %, or about 1 to about 15 wt. % of one or more water-soluble solvents comprising polyhydric alcohols selected from the group consisting of glycerin, ethylhexylglycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof; and (g) about 0.1 to about 20 wt. %, about 0.5 to about 15 wt. %, or about 1 to about 15 wt. % of one or more fatty compounds selected from the group consisting of ozokerite, cetearyl alcohol, tribehenin, stearyl alcohol, petrolatum, and a mixture thereof.

The hair styling composition exhibits non-Newtonian shear thickening behavior and may be in the form of a liquid paste. Furthermore, the liquid paste may include one or more conditioning agents, for example, bis-diglyceryl polyacyladipate-2, PEG-40/PPG-8 methylaminopropyl/hydroxypropyl dimethicone copolymer, and a mixture thereof.

In another embodiment, the hair styling compositions include:
(a) about 0.1 to about 7 wt. %, about 0.5 to about 6 wt. %, and about 1 to about 5 wt. % of AMP-acrylates/allyl methacrylate copolymer;
(b) about 0.1 to about 10 wt. %, about 0.5 to about 8 wt. %, or about 1 to about 6 wt. % of polyvinylpyrrolidone/vinyl acetate (VP/VA) copolymer;
(c) about 0.01 to about 10 wt. %, about 0.05 to about 8 wt. %, or about 0.05 to about 5 wt. % of maltodextrin;
(d) about 0.1 to about 15 wt. %, about 0.1 to about 12 wt. %, or about 1 to about 10 wt. % of one or more nonionic surfactants;
(e) about 50 to about 90 wt. % of water, about 50 to about 85 wt. %, or about 55 to about 85 wt. % water;
(f) about 1 to about 25 wt. %, about 1 to about 20 wt. %, or about 1 to about 15 wt. % of one or more water-soluble solvents comprising polyhydric alcohols; and
(g) about 0.1 to about 20 wt. %, about 0.5 to about 15 wt. %, or about 1 to about 15 wt. % of one or more fatty compounds.

The hair styling composition exhibits non-Newtonian shear thickening behavior and may be in the form of a liquid clay. Furthermore, the liquid clay may include one or more conditioning agents, for example, bis-diglyceryl polyacyladipate-2, PEG-40/PPG-8 methylaminopropyl/hydroxypropyl dimethicone copolymer, lecithin, hydrogenated lecithin, and a mixture thereof.

More specifically, in some instances, the hair styling composition may include:
(a) about 0.1 to about 7 wt. %, about 0.5 to about 6 wt. %, and about 1 to about 5 wt. % of AMP-acrylates/allyl methacrylate copolymer;
(b) about 0.1 to about 10 wt. %, about 0.5 to about 8 wt. %, or about 1 to about 6 wt. % of polyvinylpyrrolidone/vinyl acetate (VP/VA) copolymer;
(c) about 0.01 to about 10 wt. %, about 0.05 to about 8 wt. %, or about 0.05 to about 5 wt. % of maltodextrin;
(d) about 0.1 to about 15 wt. %, about 0.1 to about 12 wt. %, or about 1 to about 10 wt. % of one or more nonionic surfactants selected from the group consisting of PEG-40 hydrogenated castor oil, polysorbate polyglyceryl-3 stearate, glyceryl stearate citrate, and a mixture thereof;
(e) about 50 to about 90 wt. % of water, about 50 to about 85 wt. %, or about 55 to about 85 wt. % water;
(f) about 1 to about 25 wt. %, about 1 to about 20 wt. %, or about 1 to about 15 wt. % of one or more water-soluble solvents comprising polyhydric alcohols selected from the group consisting of glycerin, ethylhexylglycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof; and
(g) about 0.1 to about 20 wt. %, about 0.5 to about 15 wt. %, or about 1 to about 15 wt. % of one or more fatty compounds selected from the group consisting of ozokerite, cetearyl alcohol, tribehenin, stearyl alcohol, petrolatum, and a mixture thereof.

The hair styling composition exhibits non-Newtonian shear thickening behavior and may be in the form of a liquid clay. Furthermore, the liquid clay may include one or more conditioning agents, for example, bis-diglyceryl polyacyladipate-2, PEG-40/PPG-8 methylaminopropyl/hydroxypropyl dimethicone copolymer, lecithin, hydrogenated lecithin, and a mixture thereof.

In another embodiment, the hair styling compositions include:
(a) about 0.1 to about 7 wt. %, about 0.5 to about 6 wt. %, and about 1 to about 5 wt. % of AMP-acrylates/allyl methacrylate copolymer;
(b) about 0.1 to about 10 wt. %, about 0.5 to about 8 wt. %, or about 1 to about 6 wt. % of polyvinylpyrrolidone/vinyl acetate (VP/VA) copolymer;
(c) about 0.01 to about 10 wt. %, about 0.05 to about 8 wt. %, or about 0.05 to about 5 wt. % of maltodextrin;
(d) about 0.1 to about 20 wt. %, about 1 to about 15 wt. %, or about 1 to about 12 wt. % of one or more nonionic surfactants;
(e) about 50 to about 90 wt. % of water, about 50 to about 85 wt. %, or about 55 to about 85 wt. % water;
(f) about 1 to about 25 wt. %, about 1 to about 20 wt. %, or about 1 to about 15 wt. % of one or more water-soluble solvents comprising polyhydric alcohols; and
(g) about 0.1 to about 25 wt. %, about 0.5 to about 20 wt. %, or about 1 to about 15 wt. % of one or more fatty compounds.

The hair styling composition exhibits non-Newtonian shear thickening behavior and may be in the form of a liquid pomade. Furthermore, the liquid pomade may include one or more conditioning agents, for example, octyldodecyl neopentanoate and/or one or more silicones, for example, dimethicone.

More specifically, in some instances, the hair styling composition may include:
(a) about 0.1 to about 7 wt. %, about 0.5 to about 6 wt. %, and about 1 to about 5 wt. % of AMP-acrylates/allyl methacrylate copolymer;
(b) about 0.1 to about 10 wt. %, about 0.5 to about 8 wt. %, or about 1 to about 6 wt. % of polyvinylpyrrolidone/vinyl acetate (VP/VA) copolymer;
(c) about 0.01 to about 10 wt. %, about 0.05 to about 8 wt. %, or about 0.05 to about 5 wt. % of maltodextrin;
(d) about 0.1 to about 20 wt. %, about 1 to about 15 wt. %, or about 1 to about 12 wt. % of one or more nonionic surfactants selected from the group consisting of laureth-7, steareth-20, PPG-5-ceteth-20, oleth-10 phosphate, PEG-4-hydrogenated castor oil, and a mixture thereof;
(e) about 50 to about 90 wt. % of water, about 50 to about 85 wt. %, or about 55 to about 85 wt. % water;
(f) about 1 to about 25 wt. %, about 1 to about 20 wt. %, or about 1 to about 15 wt. % of one or more water-soluble solvents comprising polyhydric alcohols selected from the group consisting of glycerin, ethylhexylglycerin, ethylene glycol, diethylene glycol, triethylene glycol, propylene glycol, dipropylene glycol, tripropylene glycol, 1,3-butanediol, 2,3-butanediol, 1,4-butanediol, 3-methyl-1,3-butanediol, 1,5-pentanediol, tetraethylene glycol, 1,6-hexanediol, 2-methyl-2,4-pentanediol, polyethylene glycol, 1,2,4-butanetriol, 1,2,6-hexanetriol, and a mixture thereof; and
(g) about 0.1 to about 25 wt. %, about 0.5 to about 20 wt. %, or about 1 to about 15 wt. % of one or more fatty compounds selected from the group consisting of C12-14 isoparaffin, C12-15 alkyl benzoate, and a mixture thereof.

The hair styling composition exhibits non-Newtonian shear thickening behavior and may be in the form of a liquid pomade. Furthermore, the liquid pomade may include one or more conditioning agents, for example, octyldodecyl neopentanoate and/or one or more silicones, for example, dimethicone.

The hair stylings compositions may be used in various methods for treating hair, for example, human hair, including human hair one an individual's head. For example, the hair styling compositions are useful for: (i) improving or retaining curl definition or hold of hair; (ii) styling and shaping the hair; (iii) providing hair fiber alignment and discipline; and (iv) improving the appearance of hair; wherein the methods typically comprise applying a hair styling composition disclosed herein to the hair.

In some instances, the hair styling composition is applied to the hand, for example, to the fingers, and the hands are sued to the apply the styling composition to the hair. In other words, a sufficient amount of hair styling composition may be deposited into the hands or onto the fingers, the hand may rubbed together to disperse the hair styling compositions (which provides shear stress which thickens the compositions), and the fingers are used to apply the hair styling composition to the hair. Upon application, the fingers/hand can be used to manipulate and style the hair.

Implementation of the present disclosure is provided by way of the following examples. The examples serve to illustrate the technology without being limiting in nature.

Example 1

(Liquid Gel)
Liquid Gel

|  | INCI US Name | A Wt. % |
|---|---|---|
| Anionic Film-Forming Polymer | AMP-ACRYLATES/ALLYL METHACRYLATE COPOLYMER | 2 |
| Nonionic Film-Forming Polymer | VP/VA COPOLYMER | 2.5 |
| Polysaccharide | MALTODEXTRIN | 0.1 |
| Water-Soluble Solvents | HEXYLENE GLYCOL | 2.5 |
|  | BUTYLENE GLYCOL | 2.5 |
|  | ETHYLHEXYLGLYCERIN | 0.1 |
| Nonionic surfactant | PEG-40 HYDROGENATED CASTOR OIL | 1.2 |
| Miscellaneous | FRAGRANCE, PRESERVATIVES, AND EXTRACTS | ≤3 |
| Carrier | WATER | QS 100 |

Example 2

(Liquid Paste)
Liquid Paste

|  | INCI US Name | B Wt. % | C Wt. % |
|---|---|---|---|
| Anionic Film-Forming Polymer | AMP-ACRYLATES/ALLYL METHACRYLATE COPOLYMER | 2 | 1 |
| Nonionic Film-Forming Polymer | VP/VA COPOLYMER | 3.8 |  |
| Amphoteric Film-Forming Polymer | OCTYLACRYLAMIDE/ACRYLATES/BUTYL AMINOETHYL METHACRYLATE COPOLYMER | — | 3 |
| Polysaccharide | MALTODEXTRIN | 0.3 | 3.7 |
| Water-Soluble Solvents | ETHYLHEXYLGLYCERIN | 0.1 | 0.1 |
|  | DIPROPYLENE GLYCOL | 0.033 | 0.055 |
|  | BUTYLENE GLYCOL | 2.5 | 5 |
|  | GLYCERIN | 0.1 | 0.2 |
| Solid Fatty Compound | OZOKERITE | 1 |  |
|  | CETEARYL ALCOHOL | 1.4 | 1 |
|  | TRIBEHENIN | 1 |  |
|  | STEARYL ALCOHOL | 2 | 1.5 |
|  | PETROLATUM | 4 | 2 |
| Conditioning Agent | BIS-DIGLYCERYL POLYACYLADIPATE-2 | 1 | 0.4 |
|  | PEG-40/PPG-8 METHYLAMINOPROPYL/ HYDROXYPROPYL DIMETHICONE COPOLYMER | 0.1 | 0.2 |
| Nonionic surfactants | STEARETH-2 | — | 2 |
|  | STEARETH-20 | — | 3.7 |
|  | PEG-40 HYDROGENATED CASTOR OIL | 2 |  |
|  | POLYSORBATE 60 | 0.3 |  |
| Miscellaneous | FRAGRANCE, PRESERVATIVES, AND EXTRACTS | ≤3 | ≤3 |
| Carrier | WATER | QS 100 | QS 100 |

Example 3

(Liquid Clay)
Liquid Clay

| | INCI US Name | D Wt. % |
|---|---|---|
| Anionic Film-Forming Polymer | AMP-ACRYLATES/ALLYL METHACRYLATE COPOLYMER | 2 |
| | SODIUM ACRYLATES COPOLYMER | 0.2 |
| Nonionic Film-Forming Polymer | VP/VA COPOLYMER | 2.5 |
| Polysaccharide | MALTODEXTRIN | 0.5 |
| Water-Soluble Solvents | DIPROPYLENE GLYCOL | 0.06 |
| | ETHYLHEXYLGLYCERIN | 0.1 |
| | BUTYLENE GLYCOL | 5 |
| | GLYCERIN | 0.2 |
| Solid Fatty Compounds | OZOKERITE | 1 |
| | CETEARYL ALCOHOL | 1.4 |
| | TRIBEHENIN | 1 |
| | STEARYL ALCOHOL | 2 |
| | PETROLATUM | 2 |
| Conditioning Agents | BIS-DIGLYCERYL POLYACYLADIPATE-2 | 1 |
| | PEG-40/PPG-8 METHYLAMINOPROPYL/ HYDROXYPROPYL DIMETHICONE COPOLYMER | 0.2 |
| | HYDROGENATED LECITHIN AND LECITHIN | 0.9 |
| Nonionic surfactant | PEG-40 HYDROGENATED CASTOR OIL | 2.5 |
| | POLYSORBATE 60 | 0.3 |
| | POLYGLYCERYL-3 STEARATE | 1.2 |
| | GLYCERYL STEARATE CITRATE | 2 |
| Miscellaneous | FRAGRANCE, PRESERVATIVES, COLORANTS, AND EXTRACTS | ≤3 |
| Carrier | WATER | QS 100 |

Example 4

(Liquid Pomade)
Liquid Pomade

| | INCI US Name | E Wt. % |
|---|---|---|
| Anionic Film-Forming Polymer | AMP-ACRYLATES/ALLYL METHACRYLATE COPOLYMER | 2 |
| Nonionic Film-Forming Polymer | VP/VA COPOLYMER | 2.5 |
| Anionic Copolymer | ACRYLATES/C10-30 ALKYL ACRYLATE CROSSPOLYMER | 0.1 |
| | POLYACRYLAMIDE | 0.2 |
| Polysaccharide | MALTODEXTRIN | 0.1 |
| Base | TRIETHANOLAMINE | 0.1 |
| Water-Soluble Solvent | HEXYLENE GLYCOL | 2.5 |
| | BUTYLENE GLYCOL | 2.5 |
| Conditioning Agent | OCTYLDODECYL NEOPENTANOATE | 1 |
| Nonionic Surfactants | LAURETH-7 | 0.04 |
| | STEARETH-20 | 4 |
| | PPG-5-CETETH-20 | 5 |
| | OLETH-10 PHOSPHATE | 3.5 |
| | PEG-40 HYDROGENATED CASTOR OIL | 2 |
| Silicone | DIMETHICONE | 1 |
| Liquid Fatty Compound | C13-14 ISOPARAFFIN | 0.1 |
| | C12-15 ALKYL BENZOATE | 1 |
| Miscellaneous | FRAGRANCE, PRESERVATIVES, pH MODIFIERS, AND EXRACTS | ≤3 |
| | WATER | QS 100 |

Example 5

(Liquid Gel)
Liquid Gel

| | INCI US Name | F Wt. % |
|---|---|---|
| Anionic Film-Forming Polymer | AMP-ACRYLATES/ALLYL METHACRYLATE COPOLYMER | 1 |
| Ampohteric Film-Forming Polymer | OCTYLACRYLAMIDE/ ACRYLATES/BUTYLAMINOETHYL METHACRYLATE COPOLYMER | 3 |
| Polysaccharide | INULIN | 0.5 |
| Base | AMINOMETHYL PROPANOL | 0.6 |
| Water-Soluble Solvent | CAPRYLYL GLYCOL | 0.4 |
| | PROPYLENE GLYCOL | 0.9 |
| Nonionic Surfactants | OLETH-10 | 1.2 |
| | POLYSORBATE 20 | 0.3 |
| Silicone | DIMETHICONE | 1.1 |
| Miscellaneous | FRAGRANCE, PRESERVATIVES, pH MODIFIERS, AND EXRACTS | ≤3 |
| | WATER | QS 100 |

Example 6

(Consumer Testing with Liquid Paste)

| Attribute | Composition B | Commercial Benchmark Product | P-Value | Sig |
|---|---|---|---|---|
| APPLICATION | | | | |
| Type of Styling Product (1-7) | 3.00 (lotion) | 5.92 (paste) | 0.0001 | *** |
| Amount Used in Grams | 0.96 | 0.54 | 0.0004 | *** |
| Consistency (0-5) | 1.46 | 4.17 | 0.0001 | *** |
| Feel on Hands (1-5) | 2.00 (slippery) | 3.83 (waxy) | 0.0001 | *** |
| Melting on Hands (1-4) | 3.00 | 2.00 | 0.0001 | *** |
| Absorption (0-5) | 2.83 | 2.50 | 0.1661 | * |
| Dist to the Ends (1-4) | 3.08 | 2.00 | 0.0001 | *** |
| Ease of Spiking/Sculpting/Shaping (1-4) | 3.58 | 3.00 | 0.0024 | *** |
| Clumping Ability (1-4) | 3.25 | 3.08 | 0.1661 | * |
| Thick Clumps (0-5) | 1.79 | 3.00 | 0.0001 | *** |
| Fast Fixing/Setting (0-5) | 3.63 | 2.75 | 0.0004 | *** |

-continued

| (Consumer Testing with Liquid Paste) | | | | |
|---|---|---|---|---|
| Attribute | Composition B | Commercial Benchmark Product | P-Value | Sig |
| POST APPLICATION | | | | |
| Model Frag. Level (1-5) | 2.83 | 3.67 | 0.0020 | *** |
| Model Pleasant Frag (1-4) | 2.50 | 1.92 | 0.0891 | ** |
| Clean Hands (1-4) | 2.67 | 1.92 | 0.0001 | *** |
| Hands - Ease of Removal (1-4) | 2.00 | 3.00 | 0.0001 | *** |
| AFTER HAIR IS DRY | | | | |
| Wet Looking Hair (0-5) | 0.00 | 0.25 | 0.0819 | ** |
| Clean Hair (1-4) | 2.33 | 1.83 | 0.0069 | *** |
| Style/Shape Control (1-10) | 4.88 | 3.13 | 0.0001 | *** |
| Thick Clumps (0-5) | 1.79 | 2.96 | 0.0001 | *** |
| Root Lift (1-4) | 3.00 | 2.25 | 0.0001 | *** |
| Coating - Initial (0-5) | 2.25 | 2.75 | 0.0069 | *** |
| Model Pref (1-2) | 1.83 | 1.25 | 0.0116 | *** |
| ELIMINATION | | | | |
| Sticky Hair (1-4) | 2.08 | 2.58 | 0.0819 | ** |
| Ability to Separate Strands (0-5) | 3.25 | 2.71 | 0.1028 | * |
| Dryness - Touch (0-5) | 0.96 | 0.17 | 0.0015 | *** |
| Coating - Elimination (1-4) | 2.17 | 2.67 | 0.0261 | *** |
| Type of Coating - Elimination (1-6) | 3.00 (waxy) | 3.92 (greasy) | 0.0001 | *** |
| Clean Hair (1-4) | 1.83 | 1.33 | 0.0069 | *** |
| Style Memory (0-5) | 3.96 | 2.71 | 0.0001 | *** |
| Model Pref (1-2) | 2.00 | 1.33 | 0.0007 | *** |

A liquid paste according to the instant disclosure (Composition B of Example 2) was subjected to consumer testing. Twelve (12) individuals compared Composition B with a commercial benchmark product (AXE® Messy Whatever Look Paste) and evaluated both products for a number of cosmetic factors. The individuals ranked the cosmetic factors numerically where lower numbers represent less or worse results and higher numbers represent more or better results. Differences between the rankings for Composition B and for the commercial benchmark product were compared to determine whether the difference was statistically significant. A difference of 0.5-1.0 was considered "slight." A difference of 1.0-1.5 was considered "noticeable." A difference of 1.5 to 2.0 was considered "dramatic." Differences found to be statistically significant are provided in the table below.

The data show that overall inventive Composition B has an advantage compared to the commercial benchmark product. For example, the results indicate that during application, there is a dramatic difference in terms of the type of styling product, consistency and feel on the hands. The commercial benchmark product was rated as having a thicker consistency that is typical of a traditional paste with a waxy/grip feel on the hands. Inventive Composition B, however, was described as being more like a lotion, with a thinner consistency and a slippery feel on the hands. Additionally, inventive Composition B distributed slightly better to the ends of the hairs, fixes/sets quicker, and does not have the thick clumping that was associated with the commercial benchmark product.

Post application results are also slightly better for inventive Composition B, for example, in terms of the hands feeling cleaner. However, the commercial benchmark product was reported to be easier to rinse from the hands. Once hair is dry, inventive Composition B exhibited higher ratings, particularly for the key attribute of style/shape control. Additionally, inventive Composition B ranked higher for clean hair, root lift and less coating. The commercial benchmark product continued to have noticeably thicker clumping (which was also noticed during application). During elimination, the results show that inventive Composition B is less sticky, easier to separate strands, less coated (waxy vs. greasy) and has cleaner hair. Additionally, inventive Composition B provided noticeably higher ratings for the Key attribute of style memory, even though it was rated as slightly higher for the attribute of drier hair.

In sum, inventive Composition B outperformed the commercial benchmark product in the key attribute of "style and shape control," an attribute that is extremely important for hair styling products. Additionally, inventive Composition B was ranked overall as being preferred to the commercial benchmark product.

Example 7

| (Consumer Testing with Liquid Clay) | | | | |
|---|---|---|---|---|
| Attribute | Inventive Composition D | Commercial Benchmark Product | P-Value | Sig |
| APPLICATION | | | | |
| Type of Styling Product (1-7) | 4.08 | 5.75 | 0.0001 | *** |
| Amount Used in Grams | 1.38 | 0.75 | 0.0029 | *** |
| Consistency (0-5) | 2.25 | 3.75 | 0.0001 | *** |
| Melting on Hands (1-4) | 2.58 | 2.00 | 0.0463 | ** |
| Dist to the Ends (1-4) | 3.25 | 2.75 | 0.0819 | * |
| DRYING | | | | |
| Fast Fixing/Setting (0-5) | 3.25 | 2.38 | 0.0013 | *** |
| Visual - Fast Drying (1-4) | 3.17 | 2.58 | 0.0674 | * |
| Model Pleasant Frag (1-4) | 3.00 | 2.17 | 0.0341 | ** |
| Hands - Ease of Removal (1-4) | 2.75 | 3.17 | 0.0172 | ** |

-continued

| (Consumer Testing with Liquid Clay) | | | | |
|---|---|---|---|---|
| Attribute | Inventive Composition D | Commercial Benchmark Product | P-Value | Sig |
| AFTER HAIR IS DRY | | | | |
| Wet Looking Hair (0-5) | 1.25 | 1.96 | 0.0187 | ** |
| Shine (1-6) | 2.83 | 3.42 | 0.0116 | ** |
| Stiffness (0-5) | 2.54 | 1.42 | 0.0001 | *** |
| Presence of Clumps (1-4) | 2.75 | 3.33 | 0.0116 | ** |
| Dryness - Touch (0-5) | 1.67 | 0.63 | 0.0064 | *** |
| Dry Ends - Visual (1-4) | 1.58 | 1.08 | 0.0527 | * |
| Type of Coating - Elimination (1-6) | 2.00 | 3.00 | 0.0204 | ** |

A liquid clay according to the instant disclosure (Composition D of Example 3) was subjected to consumer testing. Twelve (12) individuals compared Composition B with a commercial benchmark product (American Crew® Molding Clay) and evaluated both products for a number of cosmetic factors. The individuals ranked the cosmetic factors numerically where lower numbers represent less or worse results and higher numbers represent more or better results. Differences between the rankings for Composition B and for the commercial benchmark product were compared to determine whether the difference was statistically significant. A difference of 0.5-1.0 was considered "slight." A difference of 1.0-1.5 was considered "noticeable." A difference of 1.5 to 2.0 was considered "dramatic." Differences found to be statistically significant are provided in the table below.

Overall, inventive Composition D and the commercial benchmark product were rated similarly—both products provided good styling benefits. For example, there were no significant differences for hold, style/shape control, and style memory. Additionally, crust type was rated flexible for both. In terms of ease of styling, both performed similarly but inventive Composition D was ranked higher for fast fixing/setting. Differences were found in terms of type of styling product and consistency. As expected, inventive composition D was not as thick as the commercial benchmark product; this was expected because inventive composition D is a "liquid clay" that exhibits shear thickening properties. Inventive Composition D was ranked higher for stiffness and dry hair feel. The type of coating for inventive Composition D was described as slippery and the commercial benchmark product was described as waxy.

The foregoing description illustrates and describes the disclosure. Additionally, the disclosure shows and describes only the preferred embodiments but, as mentioned above, it is to be understood that it is capable to use in various other combinations, modifications, and environments and is capable of changes or modifications within the scope of the invention concepts as expressed herein, commensurate with the above teachings and/or the skill or knowledge of the relevant art. The embodiments described herein above are further intended to explain best modes known by applicant and to enable others skilled in the art to utilize the disclosure in such, or other, embodiments and with the various modifications required by the particular applications or uses thereof. Accordingly, the description is not intended to limit the invention to the form disclosed herein. Also, it is intended to the appended claims be construed to include alternative embodiments.

As used herein, the terms "comprising," "having," and "including" are used in their open, non-limiting sense.

The terms "a," "an," and "the" are understood to encompass the plural as well as the singular. Thus, the term "a mixture thereof" also relates to "mixtures thereof." Throughout the disclosure, the term "a mixture thereof" is used, following a list of elements as shown in the following example where letters A-F represent the elements: "one or more elements selected from the group consisting of A, B, C, D, E, F, and a mixture thereof." The term, "a mixture thereof" does not require that the mixture include all of A, B, C, D, E, and F (although all of A, B, C, D, E, and F may be included). Rather, it indicates that a mixture of any two or more of A, B, C, D, E, and F can be included. In other words, it is equivalent to the phrase "one or more elements selected from the group consisting of A, B, C, D, E, F, and a mixture of any two or more of A, B, C, D, E, and F."

Likewise, the term "a salt thereof" also relates to "salts thereof." Thus, where the disclosure refers to "an element selected from the group consisting of A, B, C, D, E, F, a salt thereof, and a mixture thereof," it indicates that that one or more of A, B, C, D, and F may be included, one or more of a salt of A, a salt of B, a salt of C, a salt of D, a salt of E, and a salt of F may be include, or a mixture of any two of A, B, C, D, E, F, a salt of A, a salt of B, a salt of C, a salt of D, a salt of E, and a salt of F may be included.

The expression "one or more" means "at least one" and thus includes individual components as well as mixtures/combinations.

Other than in the operating examples, or where otherwise indicated, all numbers expressing quantities of ingredients and/or reaction conditions may be modified in all instances by the term "about," meaning within +/−5% of the indicated number.

All percentages, parts and ratios herein are based upon the total weight of the compositions of the present invention, unless otherwise indicated.

Some of the various categories of components identified may overlap. In such cases where overlap may exist and the composition includes both components (or the composition includes more than two components that overlap), an overlapping compound does not represent more than one component. For example, certain compounds may be considered both an emulsifier and a fatty compound. If a particular composition includes both an emulsifier and a fatty compound, a single compound will serve as only the emulsifier or the fatty compound (the single compound does not serve as both the emulsifier and the fatty component).

A "rinse-off" product refers to a composition that is rinsed and/or washed from the hair with water either after or during the application of the composition onto the hair, and before drying and/or styling the hair. At least a portion of the composition is removed from the hair during the rinsing and/or washing.

A "leave-on" product refers to a composition that is not rinsed and/or washed from the hair after or during application of the composition onto the hair. The composition remains on the hair during drying and/or styling.

As used herein, all ranges provided are meant to include every specific range within, and combination of sub ranges between, the given ranges. Thus, a range from 1-5, includes specifically 1, 2, 3, 4 and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 2% by weight of a specific material added to a composition, based on the total weight of the compositions. Nonetheless, the compositions may include less than about 1 wt. %, less than about 0.5 wt. %, less than about 0.1 wt. %, or none of the specified material. All of the components set forth herein may be optionally included or excluded from the compositions/method/kits. When excluded, the compositions/methods/kits may be free or essentially free of the component. For example, a particular composition may be free or essentially free of alkoxylated compounds, for example, ethoxylated thickeners and/or ethoxylated surfactants. Likewise, a particular composition may be free or essentially free of sulfates, such as sulfate surfactants.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The invention claimed is:

1. A liquid-to-solid transforming hair styling composition comprising:
   (a) about 0.1 to about 7 wt. % of AMP-acrylates/allyl methacrylate copolymer, based on the total weight of the hair styling composition;
   (b) one or more nonionic film-forming polymers and/or amphoteric film-forming polymer;
   (c) about 0.01 to about 10 wt. % of one or more polysaccharides;
   (d) one or more nonionic surfactants; and
   (e) water;
   wherein the hair styling composition exhibits non-Newtonian shear thickening behavior and has a viscosity of about 5000 mPas (cP) or less at room temperature (25° C.) (Torque 36.5% RPM 10, Spindle 3).

2. The hair styling composition of claim 1 comprising one or more nonionic film-forming polymers.

3. The hair styling composition of claim 2, wherein the one or more nonionic film-forming polymers are selected from the group consisting of vinylpyrrolidone homopolymers and copolymers of vinylpyrrolidone and of vinyl acetate.

4. The hair styling composition of claim 1, wherein the one or more polysaccharides comprises maltodextrin, gum arabics, or a combination thereof.

5. The hair styling composition of claim 1, wherein the one or more nonionic surfactants are selected from the group consisting of polysorbates, hydrogenated castor oil, ethylene glycol ethers of fatty alcohols, polyethylene glycol derivatives of glycerides, polyoxyethylene alkyl ethers, alkyl polysaccharides, esters of polyols with fatty acids and alkoxylated derivatives thereof.

6. The hair styling composition of claim 1 comprising about 1 to about 20 wt. % of the one or more nonionic surfactants.

7. The hair styling composition of claim 1, further comprising:
   (f) one or more water-soluble solvents.

8. The hair styling composition of claim 7, wherein the one or more water-soluble solvents are selected from the group consisting of polyhydric alcohols, glycol ethers, $C_{1-4}$ alcohols, and a mixture thereof.

9. The hair styling composition of claim 7 comprising about 1 to about 20 wt. % of the one or more water-soluble solvents.

10. The hair styling composition of claim 1, further comprising:
    (g) one or more fatty compounds.

11. The hair styling composition of claim 10, wherein the one or more fatty compounds are selected from the group consisting of oils, mineral oils, vegetable oils, fatty alcohols, fatty acids, hydroxy-substituted fatty acids, waxes, triglycerides, lanolins, alkanes, petrolatum, paraffins, and a mixture thereof.

12. The hair styling composition of claim 10 comprising about 1 to about 0.1 to about 20 wt. % of the one or more fatty compounds.

13. The hair styling composition of claim 1 comprising one or more amphoteric film-forming polymers.

14. The hair styling composition of claim 13, wherein the one or more amphoteric film-forming polymers comprises octylacrylamide/acrylates/butylaminoethyl methacrylate copolymer.

15. The hair styling composition of claim 13 comprising about 0.5 to about 15 wt. % of the one or more amphoteric film-forming polymers.

16. A method of styling hair comprising applying a hair styling composition of claim 1 to the hair.

17. The composition of claim 4, wherein the hair the one or more polysaccharides comprises gum arabics.

18. A liquid-to-solid transforming hair styling composition comprising:
    (a) about 0.1 to about 7 wt. % of AMP-acrylates/allyl methacrylate copolymer, based on the total weight of the hair styling composition;
    (b) one or more amphoteric film-forming polymer;
    (c) about 0.01 to about 10 wt. % of gum arabics;
    (d) one or more nonionic surfactants; and
    (e) water;
    wherein the hair styling composition exhibits non-Newtonian shear thickening behavior and has a viscosity of about 5000 mPas (cP) or less at room temperature (25° C.) (Torque 36.5% RPM 10, Spindle 3).

19. The hair styling composition of claim 18, wherein the one or more amphoteric film-forming polymers comprises octylacrylamide/acrylates/butylaminoethyl methacrylate copolymer.

20. A liquid-to-solid transforming hair styling composition comprising:
    (a) about 0.1 to about 7 wt. % of AMP-acrylates/allyl methacrylate copolymer, based on the total weight of the hair styling composition;
    (b) about 0.5 to about 15 wt. % of octylacrylamide/acrylates/butylaminoethyl methacrylate copolymer;
    (c) about 0.01 to about 10 wt. % of gum arabics;
    (d) about 1 to about 20 wt. % of one or more nonionic surfactants;
    (e) water; and
    (f) about 1 to about 20 wt. % of one or more water-soluble solvents chosen from polyhydric alcohols, glycol ethers, $C_{14}$ alcohols, and a mixture thereof;
    wherein the hair styling composition exhibits non-Newtonian shear thickening behavior and has a viscosity of about 5000 mPas (cP) or less at room temperature (25° C.) (Torque 36.5% RPM 10, Spindle 3).

* * * * *